(12) United States Patent
Hauser et al.

(10) Patent No.: US 9,752,939 B2
(45) Date of Patent: Sep. 5, 2017

(54) MEASURING DEVICE AND MEASURING METHOD FOR REGISTERING AN AMBIENT TEMPERATURE OF A MEDICAL MACHINE, AND DEVICE AND METHOD FOR MEDICAL INSUFFLATION

(71) Applicants: Walter Hauser, Schaffhausen (CH); Manfred Schmidt, Allensbach (DE); Otmar Stillhard, Steckborn (CH)

(72) Inventors: Walter Hauser, Schaffhausen (CH); Manfred Schmidt, Allensbach (DE); Otmar Stillhard, Steckborn (CH)

(73) Assignee: Storz Endoskop Produktions GmbH, Tuttlingen (DE)

( * ) Notice: Subject to any disclaimer, the term of this patent is extended or adjusted under 35 U.S.C. 154(b) by 265 days.

(21) Appl. No.: 14/636,678

(22) Filed: Mar. 3, 2015

(65) Prior Publication Data
US 2015/0253205 A1    Sep. 10, 2015

(30) Foreign Application Priority Data

Mar. 4, 2014 (DE) .......................... 10 2014 002 762
Feb. 20, 2015 (EP) ..................................... 15000498

(51) Int. Cl.
*G01K 13/02* (2006.01)
*G01K 1/20* (2006.01)
(Continued)

(52) U.S. Cl.
CPC .......... *G01K 13/02* (2013.01); *A61M 13/003* (2013.01); *G01K 1/20* (2013.01); *G01K 7/16* (2013.01);
(Continued)

(58) Field of Classification Search
CPC .... G01K 13/02; G01K 2013/024; G01K 1/20; G01K 7/16; G01K 7/42; A61M 2205/3368; A61M 2205/3372
(Continued)

(56) References Cited

U.S. PATENT DOCUMENTS

| 4,741,476 A | 5/1988 | Russo et al. |
| 2005/0209813 A1 | 9/2005 | Kautz et al. |

(Continued)

FOREIGN PATENT DOCUMENTS

| DE | 87677 B1 | 8/1980 |
| DE | 69223723 T2 | 4/1998 |

(Continued)

OTHER PUBLICATIONS

European Search Report (Translated) Application No. 15 00 0498 Completed: Jun. 29, 2015; Mailing Date: Jul. 6, 2015 3 pages.
(Continued)

*Primary Examiner* — Lisa Caputo
*Assistant Examiner* — Philip Cotey
(74) *Attorney, Agent, or Firm* — Whitmyer IP Group LLC

(57) ABSTRACT

A measuring device and method according to the invention for registering an ambient temperature $T_a$ of a medical machine including a measuring housing, which is arranged on an outer wall of the machine and in which at least one temperature sensor remote from the machine and at least one temperature sensor (16, 16') near to the machine are held, wherein the at least one temperature sensor remote from the machine registers a first temperature $T_1$ and the at least one temperature sensor near to the machine registers a second temperature $T_2$, and an evaluation apparatus configured to establish the ambient temperature $T_a$ using a difference between the first temperature $T_1$ registered by the at least one temperature sensor remote from the machine and the second (Continued)

temperature $T_2$ registered by the at least one temperature sensor near to the machine.

20 Claims, 2 Drawing Sheets

(51) Int. Cl.
*G01K 7/42* (2006.01)
*A61M 13/00* (2006.01)
*G01K 7/16* (2006.01)

(52) U.S. Cl.
CPC ....... *G01K 7/42* (2013.01); *A61M 2205/3368* (2013.01); *A61M 2205/3372* (2013.01); *A61M 2205/36* (2013.01); *A61M 2209/02* (2013.01); *G01K 2013/024* (2013.01)

(58) Field of Classification Search
USPC .......................................................... 374/170
See application file for complete search history.

(56) References Cited

U.S. PATENT DOCUMENTS

| | | | | |
|---|---|---|---|---|
| 2009/0144014 A1* | 6/2009 | Aljabari | .................... | G01K 1/20 |
| | | | | 702/130 |
| 2010/0128754 A1* | 5/2010 | Jetter | ................. | A61B 5/14532 |
| | | | | 374/110 |
| 2011/0119018 A1* | 5/2011 | Skarp | ....................... | G01K 7/42 |
| | | | | 702/130 |
| 2012/0095312 A1* | 4/2012 | Ramey | ................... | A61B 5/002 |
| | | | | 600/365 |
| 2012/0277673 A1 | 11/2012 | Levin et al. | | |
| 2013/0133651 A1* | 5/2013 | Barker | ................. | A61M 16/12 |
| | | | | 128/203.14 |
| 2013/0197437 A1* | 8/2013 | Faries | ..................... | A61M 5/44 |
| | | | | 604/113 |
| 2014/0074078 A1* | 3/2014 | Kumar | ................... | A61B 10/00 |
| | | | | 606/15 |

FOREIGN PATENT DOCUMENTS

| | | |
|---|---|---|
| DE | 19800753 A1 | 7/1999 |
| DE | 102005049676 B3 | 11/2006 |
| DE | 102006019402 A1 | 10/2007 |
| EP | 0564953 A1 | 10/1993 |
| GB | 2131175 A | 6/1984 |
| WO | 2010023255 A1 | 3/2010 |

OTHER PUBLICATIONS

European Search Report Application No. 15 00 0498 Completed: Jun. 29, 2015; Mailing Date: Jul. 6, 2015 7 pages.

* cited by examiner

MEASURING DEVICE AND MEASURING METHOD FOR REGISTERING AN AMBIENT TEMPERATURE OF A MEDICAL MACHINE, AND DEVICE AND METHOD FOR MEDICAL INSUFFLATION

FIELD OF THE INVENTION

The present invention relates to a measuring device and a measuring method for registering an ambient temperature of a medical machine, and to a device and a method for medical insufflation.

BACKGROUND OF THE INVENTION

EP 0 564 953 A1 has disclosed the practice of using a heating tube, provided with a heating wire coil, during an insufflation of $CO_2$ or $N_2O$ gas into a biological body, wherein the gas is guided to an insufflation instrument through said heating tube and heated to approximately the body temperature of the patient in the process. A temperature sensing device is integrated into the distal region of the heating tube. The temperature of a gas volume supplied to the body, which was registered by the temperature sensor, can no longer be modified by the heating provided in the heating tube; all that can be modified is the temperature of a subsequently supplied gas volume.

In accordance with DE 10 2006 019 402 A1, the gas supplied to a patient in the case of a machine for transnasal insufflation (TNI) is heated to a temperature lying approximately 10 K above the ambient temperature. Depending on the ambient temperature registered by an ambient temperature sensor, an intended gas temperature of the gas at the outlet of a humidifier is determined and a heating power of the humidifier heating is controlled in such a way that an actual gas temperature is as close as possible to the intended gas temperature.

In accordance with DE 692 23 723 T2, the ambient temperature of the surrounding atmosphere is registered in a respiratory air humidifier comprising an ambient temperature sensing device, and a gas outlet temperature is calculated depending on the ambient temperature in order to selectively supply heating means with energy so as to reduce the condensation of the moistened gas.

DE 10 2005 049 676 63 has disclosed a method for contactless determination of the body core temperature of a human, wherein the surface temperature of the human is registered at a body measurement point by means of a temperature sensor unit arranged at a distance from same and the sensor signal is transmitted to an evaluation unit. The body core temperature is deduced taking into account the difference between the surface temperature and an ambient temperature, wherein the ambient temperature is regulated or stabilized to a predetermined temperature by a stabilizing device. According to WO 2010/023255 A1, a temperature of a body is measured with the aid of a first and a second temperature sensor which are enclosed in a material, wherein a contact face contacts the body and the first and the second temperature sensor are arranged at different heights over the contact face. In the aforementioned methods, an ambient temperature is not registered precisely.

DE 198 00 753 A1, which is not part of the generic prior art, discloses a sensor for a noninvasive temperature measurement of a fluid flowing in a tube, wherein the temperature of the fluid to be measured is established from the heat flow behavior of the fluid and externally measured temperatures. DD 87 677 B1, which is likewise not part of the generic prior art, describes a device for measuring the goods temperature of liquid and highly viscous masses, comprising a rod-shaped temperature sensing device which protrudes into the goods to be measured and which is connected to a thermostat, an amplifier and a display or registering machine. Here, one measuring point is provided at the tip of the temperature sensing device and another one is provided on the shaft thereof. A corrected thermoelectric voltage is established by virtue of the fact that the difference of the thermoelectric voltages, multiplied by a constant dependent on the structure and the setup of the sensing device and the goods to be measured, is added to the thermoelectric voltage at the measuring point at the sensing device tip. A thermostat is used for switching off the influence of the ambient temperature. Furthermore, GB 2 131 175 A, which is not part of the generic prior art, discloses a probe inserted into the wall of a combustion chamber, said probe comprising two elongate bodies separated from one another, which each contain a distal and a proximal temperature sensing device. The proximal end of the probe can be kept at a controlled temperature by means of a cooling liquid. An ambient temperature is not established in the aforementioned devices either.

SUMMARY OF THE INVENTION

In many medical applications, for example in gas insufflation, registration of the ambient temperature with as little falsification as possible is advantageous. Temperature sensors of different types are known; by way of example, these operate using temperature-dependent resistances or contact voltages, or are embodied as semiconductor sensors or as infrared radiation sensors. If such a sensor is used for measuring an air temperature or for measuring the temperature in the surroundings of a machine, care has to be taken that the temperature value registered by the sensor is not falsified by action of heat transmitted by a holder of the sensor or by the heat emitted by the machine during operation. Such falsification occurs, in particular, if the temperature sensor utilized for registering the ambient temperature is arranged on the machine itself. On the other hand, arranging an ambient temperature sensor at a relatively large distance from the machine, the control of which being performed using the ambient temperature established by the sensor, is inconvenient, connected with corresponding lines or signal transmission paths and error-prone. Even if this can avoid falsification of the registered temperature value by the heat generated by the machine, there nevertheless are no assurances that the temperature measured at a relatively large distance from the machine is in fact representative for the ambient temperature in a region that is relevant to the control of the machine.

It is an object of the present invention to specify a measuring device and a measuring method for registering an ambient temperature of a medical machine, wherein the aforementioned disadvantages are avoided to the greatest possible extent. In particular, it is an object of the present invention to specify a measuring device and a measuring method for registering the ambient temperature, wherein the measuring device is arranged at a medical machine generating heat. Furthermore, it is an object of the invention to specify a device and a method for medical insufflation, which are improved, particularly in view of the temperature control of the gas supplied to a patient.

This object is achieved by a measuring device in accordance with the invention.

Advantageous developments of the invention emerge from the dependent claims.

A measuring device according to the invention for registering an ambient temperature of a medical machine, for example of a medical insufflation machine, comprises a measuring housing arranged or arrangeable at an outer wall of the machine. The measuring housing is embodied, in particular, to be fastened to the outer wall of the machine or to be inserted into a recess or a through-hole in the outer wall of the machine and it can, for example, be designed in the form of a cap or sensing device protruding beyond the outer wall. The region of the outer wall of the machine, at which the measuring housing can be arranged, is preferably a front region or a front plate of the machine because, as a result of this, it is generally possible to register a temperature representative for the surroundings of the machine. In particular, the machine can be a machine emitting heat and comprising sources of heat, e.g. electrical loads, the loss heat of which during the operation leads to a thermal emission by the machine to the immediate surroundings thereof as a result of heating the outer wall of the machine. However, the machine may also have an outer wall that is colder than the surroundings, for example due to the passing of a liquid that is colder than the surroundings, and it can thereby withdraw heat from the immediate surroundings thereof. The registered ambient temperature is, in particular, an air temperature in the surroundings of the machine.

The measuring device according to the invention furthermore comprises at least one temperature sensor remote from the machine and held in the measuring housing and at least one temperature sensor near to the machine and held in the measuring housing. Therefore, the measuring device is embodied in such a way that, when it is arranged at the outer wall of the machine, the temperature sensor remote from the machine is arranged in a region of the interior of the measuring housing remote from the machine and the at least one temperature sensor near to the machine is arranged in a region of the interior of the measuring housing near to the machine or else, if the measuring housing is inserted into the outer wall of the machine, in a region of the interior of the measuring housing that is inside the machine. The at least one temperature sensor remote from the machine is provided for registering a first temperature and the at least one temperature sensor near to the machine is provided for registering a second temperature, i.e. the temperature sensors are actuatable for registering corresponding temperature values and, in particular, are electrically switched accordingly.

Furthermore, the measuring device according to the invention comprises an evaluation apparatus configured to establish the ambient temperature from a difference between the temperatures registered by the at least one temperature sensor remote from the machine and the at least one temperature sensor near to the machine. In addition to the temperature difference, one or more temperatures registered by the temperature sensors themselves can also be used when establishing the ambient temperature. In particular, the evaluation apparatus comprises a processor means, for example a microprocessor, which is programmed to establish the ambient temperature from the first and the second temperature using the difference between the first temperature and the second temperature. Preferably, the evaluation apparatus is embodied as a supply and evaluation apparatus, which supplies the temperature sensors with electric power, actuates and reads said temperature sensors for the temperature measurement and evaluates the temperature values supplied by the temperature sensors as described.

As a result of the fact that the ambient temperature is established from the temperature values that are supplied by a temperature sensor remote from the machine and by a temperature sensor near to the machine and established using a temperature difference between the temperature values, a temperature registration which is largely independent of the heat emitted by the machine or the heat withdrawn by the machine from its surroundings is successful. What was identified according to the invention is that a largely unfalsified measurement of the ambient temperature is possible by arranging at least one temperature sensor near to the machine and at least one temperature sensor remote from the machine and by evaluating the temperature gradient between the temperature sensors. Using this, a relatively accurate measurement of the surrounding temperature, which is largely uninfluenced by the immediate surroundings of the machine, still is possible, even if the machine is installed in a frame in which further heat sources are situated and/or in which the air circulation is restricted.

Advantageously, the measuring housing is made of a plastic, in particular a plastic with a low thermal conductivity and a low heat capacity. While a low thermal conductivity enables thermal decoupling from the machine, a low heat capacity enables quick equalization to the ambient temperature and therefore a quick registration of, in particular, changes in the ambient temperature.

In accordance with a preferred embodiment of the invention, the measuring housing is embodied in an elongate form and therefore in the form of a sensing device or temperature sensing device, which extends beyond the outer wall of the machine. In particular, the measuring housing is embodied with such a length that it protrudes one or a few centimeters, e.g. approximately 1.5 cm, to the outside from the outer wall of the machine if it is inserted thereon or therein. Consequently, the at least one sensor remote from the machine can be arranged in a region of the measuring housing which is only influenced a little by the surface temperature of the machine and, possibly, by a convection layer which may form on the outer wall of the machine. As a result of this, the accuracy of the registration of the ambient temperature can be improved.

Preferably, the measuring housing is embodied in a closed-off manner or embodied in an at least largely closed-off manner, at least in a region provided for the arrangement outside of the machine, i.e. in the outer region of the outer wall. The measuring housing can be largely closed-off in the interior region of the machine as well. In particular, the interior of the measuring housing may form a closed-off or largely closed-off air space. As a result of the measuring housing being closed-off at least in the outer region, it is possible to avoid a dirtying of the temperature sensors as a result of entering dust-laden air or as a result of entering liquids. Furthermore, this simplifies cleaning and the meeting of hygienic requirements in the case of medical uses, particularly when used in an operating theater.

Preferably, the measuring housing has a cylindrical embodiment in sections. As a result, it is easier to insert the measuring housing into an outer wall of the machine, in particular into a bore introduced into the outer wall. In a particularly preferred manner, the measuring housing is insertable into the bore in a closed-off manner.

Furthermore, it is advantageous if the measuring housing has a cylindrical section in the region remote from the machine, said section having a smaller diameter than a cylindrical section of the measuring housing in the region near to the machine. While the cylindrical section near to the machine, embodied with a larger diameter, enables a simple and closed-off insertion into a bore in the outer wall of the machine and ensures increased stability against inadvertent bending or breaking of the measuring housing, the region remote from the machine, embodied with a smaller diameter, is advantageous since the sensor remote from the machine arranged therein is thermally coupled more closely to the measuring housing. This further improves the thermal coupling of the temperature sensor remote from the machine to the surrounding air and, as a result of this, the accuracy of the registration of the ambient temperature is further improved.

Preferably, the at least one temperature sensor remote from the machine and/or the at least one temperature sensor near to the machine are arranged at a distance from the inner side of the measuring housing and therefore, in particular, arranged in an air space in the interior of the measuring housing, particularly preferably approximately in the center of the measuring housing or, in the case of a measuring housing that is cylindrical in sections, near the cylinder axis. As a result of this, a simpler attachment of the temperature sensors and a temperature measurement that is less sensitive to one-sided action of heat radiation thereon are made possible.

Furthermore, it is preferable for the evaluation apparatus to be held at least partly within the measuring housing, in particular in an end region of the measuring housing inside the machine. As a result of this, a compact design of the measuring device as a temperature sensing device is made possible, wherein the evaluation apparatus can be configured to supply the established value for the ambient temperature in analog or digital form. In particular, the evaluation apparatus can be embodied in such a way that the measuring device can be actuated and read like a conventional temperature sensor. Here, what was found is that establishing the ambient temperature using the temperature gradient between the temperature sensors is sufficiently robust, and so the heat development of the evaluation apparatus does not lead to a significant falsification of the established temperature value of the ambient temperature.

In a particularly preferred manner, the at least one temperature sensor remote from the machine and the at least one temperature sensor near to the machine are attached to a common carrier circuit board arranged within the measuring housing. In a further more preferable manner, the evaluation apparatus can also be arranged on the same carrier circuit board. As a result of this, a particularly simple setup and a particularly cost-effective production of the measuring device are made possible.

In accordance with a preferred embodiment of the invention the evaluation apparatus is configured in such a way that the ambient temperature is established using the difference between the temperatures registered by the at least one temperature sensor remote from the machine and the at least one temperature sensor near to the machine, and it is established further using a first and a second thermal resistance $R_{th1}$, $R_{th2}$, in particular from the ratio $R_{th1}/R_{th2}$ of the thermal resistances. Here, the first thermal resistance $R_{th1}$ represents the thermal resistance for the heat transfer from the surroundings of the machine, in particular from the surroundings of a region of the measuring housing remote from the machine, to the at least one temperature sensor remote from the machine, and the second thermal resistance $R_{th2}$ represents the thermal resistance for the heat transfer from the at least one temperature sensor remote from the machine to the at least one temperature sensor near to the machine. As a result of the fact that the thermal resistances, by means of which the temperature sensor remote from the machine is thermally coupled to the surroundings and the temperature sensor near to the machine is thermally coupled to the temperature sensor remote from the machine, are taken into account for establishing the ambient temperature, a precise establishment of the ambient temperature is made possible in a simple manner.

In accordance with a particularly preferred embodiment of the invention, the evaluation apparatus is configured to establish the ambient temperature $T_a$ in accordance with $$T_a = T_1 + k(T_1 - T_2)$$

where $$k = R_{th1}/R_{th2}.$$

In particular, the evaluation apparatus has processor means which are programmed for performing a corresponding calculation. The thermal resistances $R_{th1}$, $R_{th2}$ are constant as soon as the measuring housing is attached to the machine, in particular inserted into a bore in the outer wall, and can be established in a preceding calibration measurement. Such a calibration may be type-specific or machine-specific or else can be performed on an individual basis after inserting the measuring housing at or into the outer wall of the machine. Here, the thermal resistances can be established in a manner known per se by measuring temperature differences and heat flows, or the ratio k of the thermal resistances $R_{th1}$, $R_{th2}$ can be calculated by evaluating the temperature values supplied by the at least one temperature sensor remote from the machine and by the at least one temperature sensor near to the machine using an ambient temperature established by an external temperature sensor. By registering and evaluating the temperature gradient between the temperature sensor remote from the machine and the temperature sensor near to the machine, establishing the ambient temperature can be made possible in a simple manner and with high accuracy, taking into account the ratio of the thermal resistances $R_{th1}$, $R_{th2}$.

In a preferred manner, at least two temperature sensors remote from the machine and/or at least two temperature sensors near to the machine are provided, wherein the at least two temperature sensors remote from the machine and the at least two temperature sensors near to the machine are respectively arranged preferably closely adjacent to one another such that the temperatures registered by the at least two temperature sensors remote from the machine are practically the same and the temperatures registered by the at least two temperature sensors near to the machine are practically the same. In particular, the at least two temperature sensors remote from the machine and/or the at least two temperature sensors near to the machine and, preferably, the evaluation apparatus as well can be attached to a common carrier circuit board arranged within the measuring housing. Furthermore, the evaluation apparatus is preferably configured to generate an error signal if a deviation between the temperatures registered by the at least two temperature sensors remote from the machine is greater than a pre-determinable threshold or if a deviation between the temperatures registered by the at least two temperature sensors near to the machine is greater than the pre-determinable threshold. By way of example, a user can be informed or measures, such as e.g. switching off a heating apparatus, can be taken automatically on the basis of the error signal. If provision is made for more than one temperature sensor remote from the machine or more than one temperature sensor near to the machine, the temperature value respectively registered by one of the sensors or else a mean value of the temperatures registered by the plurality of adjacent sensors can be used to calculate the first and the second temperature. As a result of a plurality of sensors being provided in each case for a redundant temperature registration, it is not only an increase in the accuracy of the temperature measurement that is made possible but errors car also be identified and therefore the safety for the patient can be increased.

Preferably, the at least one temperature sensor remote from the machine and/or the at least one temperature sensor near to the machine is/are embodied, as a semiconductor sensor. Such semiconductor sensors are known per se and make possible an accurate and simple registration of the temperature prevailing at the location of the sensor.

In accordance with an alternative embodiment, the at least one temperature sensor remote from the machine and/or the at least one temperature sensor near to the machine is/are embodied as an infrared sensor which registers the heat radiation emitted by an inner wall of the measuring housing. To this end, the infrared sensors are directed to the inner side of the measuring housing. This enables an accurate registration of the temperature of the measuring housing.

In a further advantageous manner, at least one temperature sensor remote from the machine is embodied as a semiconductor sensor and at least one temperature sensor remote from the machine is embodied as an infrared sensor and/or at least one temperature sensor near to the machine is embodied as a semiconductor sensor and at least one temperature sensor near to the machine is embodied as an infrared sensor. As a result of this, a further improved temperature registration can be made possible.

In a measuring method according to the invention for registering an ambient temperature of a medical machine, in particular a medical machine emitting heat or a medical machine withdrawing heat from the surroundings thereof, a first temperature is measured using at least one temperature sensor remote from the machine, which temperature sensor is held in a region, remote from the machine, of a measuring housing, which is arranged on an outer wall of the machine, and a second temperature is measured using at least one temperature sensor near to the machine, which is held in a region, near to the machine, of the measuring housing. The ambient temperature is established using a difference between the temperatures registered by the at least one temperature sensor remote from the machine and the at least one temperature sensor near to the machine. Furthermore, the temperatures registered by the at least one temperature sensor remote from the machine and the at least one temperature sensor near to the machine can even be used when establishing the ambient temperature. The ambient temperature is preferably registered by a measuring device embodied as described above, which measuring device is arranged on the outer wall of the machine or inserted into the latter. As a result of such a measuring method, an accurate measurement of the ambient temperature is made possible, which measurement is largely unfalsified by heat emission or a cooling effect of the machine.

In accordance with a preferred embodiment of the measuring method according to the invention, use is moreover made of a first and a second thermal resistance for establishing the ambient temperature, wherein the at least one temperature sensor remote from the machine is thermally coupled to the surroundings of the machine, in particular to the surroundings of a region of the measuring housing arranged outside of the outer wall of the machine, via the first thermal resistance, and the at least one temperature sensor near to the machine is thermally coupled to the at least one temperature sensor remote from the machine via the second thermal resistance. Here, the ambient temperature $T_a$ is established in accordance with $$T_a = T_1 + k(T_1 - T_2)$$

where $$k = R_{th1}/R_{th2}.$$

The constant k or the two thermal resistances $R_{th1}$ and $R_{th2}$ may have been established in advance, for example during a calibration measurement, and stored in a memory for use within the scope of establishing the temperature.

A medical insufflation device according to the invention comprises a medical insufflation machine which comprises a measuring device for registering an ambient temperature, embodied as described above, or on which such a measuring device is attached. The insufflation machine is embodied in a manner known per se and can, in particular, comprise valves and/or pumps in order to supply insufflation gas, e.g. $CO_2$, to a patient at a suitable pressure and, optionally, already heated in advance. Furthermore, the insufflation device comprises an insufflation tube attachable to the insufflation machine, by means of which insufflation tube the insufflation gas s supplied from the insufflation machine to an insufflation instrument, for example to a Veress needle, which serves to introduce insufflation gas into the patient. The insufflation device furthermore comprises a heating apparatus for the temperature control of the insufflation gas supplied to the patient. The heating apparatus is preferably integrated into the insufflation tube, for the purposes of which the latter may be equipped with electric heating wires for heating the gas guided through the tube. The heating wires may have a connection which, when the tube is connected to the insufflation machine, is likewise connected thereto.

Furthermore, the medical insufflation device according to the invention comprises a control apparatus for actuating the heating apparatus. Here, the control apparatus is configured in such a way that the heating apparatus is actuated depending on the ambient temperature, which is registered as described above. In particular, the control apparatus controls or regulates the heating power of the heating apparatus in such a way that, taking into account the heat transfer, dependent on the ambient temperature, between the surrounding air and the insufflation gas when it passes through the insufflation tube on the way to the patient, the insufflation gas has a predetermined temperature when it enters the patient, which temperature for example corresponds to the body temperature of the patient. If the insufflation gas is already heated to the predetermined temperature within the insufflation machine, the heating apparatus is actuated in such a way that the gas is held at this temperature during the forwarding through the tube. Here, the heating power is controlled depending on, in particular, the gas temperature at the gas output of the insufflation machine, the gas through-flow and the ambient temperature. The control apparatus can also be embodied for controlling the further functions of the insufflation machine, for example for controlling or regulating the through-flow and the pressure.

The ambient temperature registered as described above generally corresponds, at least approximately, to the temperature in a region between the medical insufflation machine and the patient through which the insufflation tube extends. Since the question of whether, and to what extent, the temperature of the insufflation gas changes when passing through the insufflation tube depends on the ambient temperature, registering the ambient temperature allows a very exact temperature control of the insufflation gas in the tube. As a result of this, the temperature of the gas introduced into the patient can be set in an ideal way.

Preferably, the measuring device for registering the ambient temperature in a medical insufflation device comprises two temperature sensors remote from the machine and/or two temperature sensors near to the machine, the measuring device is embodied to generate an error signal for the case where a temperature difference between two adjacent sensors exceeds a threshold, and the control apparatus is configured in such a way that the heating apparatus is switched off as a result of the error signal. Furthermore, a warning signal can be output to a user in this case.

In a method according to the invention for medical insufflation, an insufflation gas is supplied to a patient in a manner known per se via an insufflation tube using an insufflation machine, for example in order to produce a cavity for performing a laparoscopic intervention. Furthermore, an ambient temperature of the insufflation machine is registered as described above and a heating apparatus is actuated depending on the ambient temperature registered thus. In particular, the heating apparatus is operated at such a heating power that, taking into account the heat transfer, dependent on the ambient temperature, between the surrounding air and the insufflation gas when it passes through the insufflation tube, the insufflation gas has a predetermined temperature when it enters the patient. As a result of this, it is possible to set the temperature of the gas introduced into the patient very precisely. Preferably, the method according to the invention for medical insufflation is performed using a device for medical insufflation embodied as described above.

Naturally, the features mentioned above and the features yet to be explained below are usable not only in the respectively specified combination, but also in other combinations or on their own without departing from the scope of the present invention.

BRIEF DESCRIPTION OF THE DRAWINGS

Further aspects of the invention emerge from the following description of preferred exemplary embodiments and the attached drawings. In detail.

DETAILED DESCRIPTION OF THE INVENTION

Figure 1:
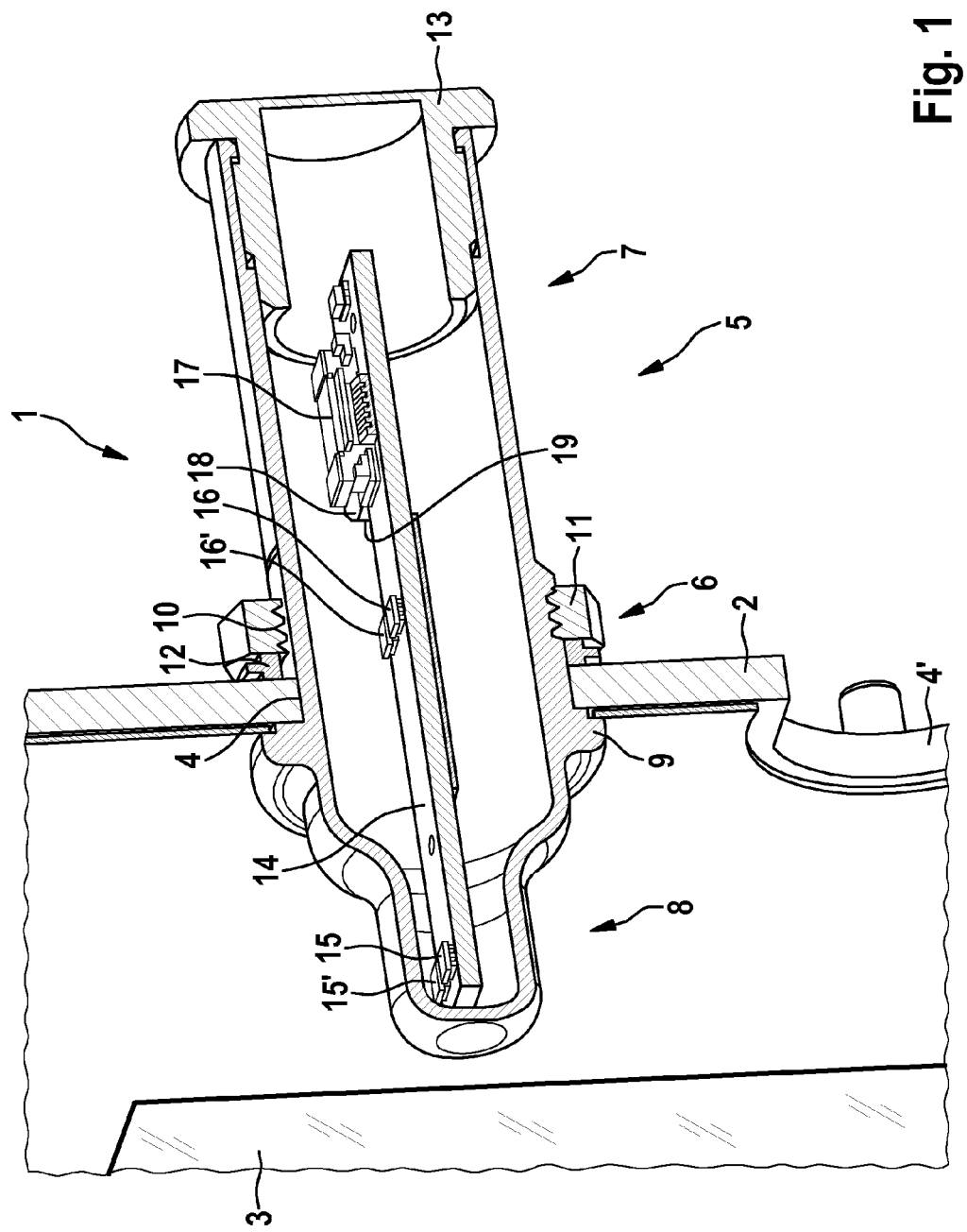
FIG. 1 shows an exemplary embodiment of a measuring device according to the invention.

As shown in FIG. 1, a measuring device for registering an ambient temperature of a machine generating heat in accordance with one embodiment of the invention is embodied as a compact temperature sensing device 1, which is inserted into a bore 4 in a front plate 2 of the machine. By way of example, the machine is a medical insufflation machine which is embodied as described with respect to FIG. 2 and the front plate 2 of which has operating and indication elements, for example a display 3. Apart from that, the machine housing is not depicted in FIG. 1. In FIG. 1, the interior of the machine is arranged to the right of the front plate 2 and the exterior space is arranged to the left of the front plate 2. The front plate 2 can have further through-holes or bores 4' for inserting further elements. The temperature sensing device 1 comprises a measuring housing 5 with connection region 6 for the connection with the front plate 2, an inner region 7, which is arranged within the machine, and an outer region 8, which is arranged outside of the machine and which, with the end region remote from the machine thereof, protrudes approximately 15 mm beyond the front plate 2. The connection region 6 has a shoulder 9, with which the measuring housing 5 rests on the front plate 2 from the outside, and a thread 10, onto which a fastening nut 11 is screwed from the inside and by means of which nut the measuring housing 5 is held securely in the bore 4 via a sealing ring 12. The measuring housing 5 is made of plastic and terminated in the end region of the inner region 7 by a plastic lid 13. The plastic lid 13 can be available as a standard part and can be inserted into the measuring housing 5 with the aid of a snap-in connection. In the end region of the outer region 8, the measuring housing 5 has a substantially cylindrical embodiment, but with a smaller diameter than in the inner region.

A carrier circuit board 14 extending in the longitudinal direction of the measuring housing 5 is held in the interior of the measuring housing 5, said carrier circuit board carrying two temperature sensors 15, 15' remote from the machine in the end region thereof remote from the machine, two temperature sensors 16, 16' near to the machine in the central region thereof and supply and evaluation electronics 17 in the end region thereof near to the machine. The temperature sensors 15, 15', 16, 16' are respectively embodied as an integrated circuit with a semiconductor temperature sensor element and connected to the supply and evaluation electronics 17 via a bus; such sensors, which supply a digital signal, are, for example, distributed by Texas Instruments under the trade name TMP106. Alternatively or additionally, provision can be made in each case for an infrared sensor which is directed to the adjacent inner wall of the measuring housing 5 (not depicted here); infrared sensors suitable for this purpose are, for example, distributed by Texas Instruments under the trade name TMP006. The two temperature sensors 15, 15' remote from the machine and the two temperature sensors 16, 16' near to the machine are respectively arranged closely adjacent to one another such that they register the same temperature. The supply and evaluation electronics 17 comprise a microprocessor and apparatuses for supplying the temperature sensors 15, 15', 16, 16' with energy. By means of a flexible circuit board 18, which extends through a through-hole 19 in the measuring housing 5, the supply and evaluation electronics 17 are connected to a control apparatus of the machine. The through-hole 19 can be closed-off by a sealing compound or a seal such that, in the case of a corresponding sealing of the plastic lid 13, the temperature sensing device 1 overall can be encapsulated.

A temperature sensing device 1 embodied thus has a compact embodiment and it is producible using methods from plastic machining and printed circuit board production known per se. Here, the measuring housing 5 is embodied as a cap, which is put onto the carrier circuit board 14 equipped with the temperature sensors 15, 15', 16, 16' and the supply and evaluation electronics 17. During the assembly of the machine, the temperature sensing device 1 is inserted into the bore 4 in the front plate 2.

The microprocessor of the supply and evaluation electronics 17 is programmed for establishing the ambient temperature $T_a$ of the machine as described below. Here, the temperature sensors 15, 15', 16, 16' are read out by the supply and evaluation electronics 17 via the bus for the purposes of registering the ambient temperature $T_a$. The mean value $T_1$ and the difference $\Delta T_1$ are established from the measured values for the temperature supplied by the two temperature sensors 15, 15' remote from the machine. Likewise, the mean value $T_2$ and the difference $\Delta T_2$ are determined from the temperature values supplied by the two temperature sensors 16, 16' near to the machine. If one of the established differences $\Delta T_1$, $\Delta T_2$ exceeds a threshold $\Delta T_s$, which is predetermined depending on the accuracy of the temperature sensors, a malfunction is assumed and the supply and evaluation electronics 17 transmit an error signal via the flexible circuit board 18 to a super-ordinate control apparatus, for example the control apparatus of the medical insufflation machine, which switches off a heating apparatus for the insufflation gas and emits a warning signal that is perceivable by a user. If neither one of the established differences $\Delta T_1$, $\Delta T_2$ exceeds the threshold $\Delta T_s$, the ambient temperature $T_a$ is calculated in accordance with $$T_a = T_1 + k(T_1 - T_2)$$

where k is a constant representing the ratio of two thermal resistances $R_{th1}$, $R_{th2}$:

$$k = R_{th1}/R_{th2}.$$

Here, $R_{th1}$ is the thermal resistance between the surroundings and the temperature sensors 15, 15' remote from the machine and $R_{th2}$ is the thermal resistance between the temperature sensors 15, 15' remote from the machine and the temperature sensors 16, 16' near to the machine. Both thermal resistances $R_{th1}$, $R_{th2}$ are respectively constant and dependent on the arrangement of the temperature sensors 15, 15', 16, 16', on the design of the measuring housing 5 and the other components of the temperature sensing device 1 and, in particular, on the utilized materials. Heat conduction in the measuring housing 5 and in the carrier circuit board 14 may play a role for the thermal resistances $R_{th1}$, $R_{th2}$, just like heat convection and heat radiation in the interior of the measuring housing 5.

In order to determine the constant k, the thermal resistances $R_{th1}$, $R_{th2}$ are established in advance, or else, as approximations for $R_{th1}$, $R_{th2}$, the thermal resistances are established between the surroundings and the outer region 8 of the temperature sensing device 1 and between the outer region 8 and the inner region 7 of the temperature sensing device 1. However, the constant k can also be determined directly by registering $T_1$ and $T_2$ when the ambient temperature $T_a$ is known. Such a determination of the constant k can be performed in a type-specific manner or individually for the temperature sensing device during a calibration measurement or else in a type-specific manner or individually in a state assembled at the machine. It was found that the thermal resistances $R_{th1}$, $R_{th2}$ and the constant k are sufficiently constant to enable a very accurate measurement of the ambient temperature $T_a$.

Figure 2:
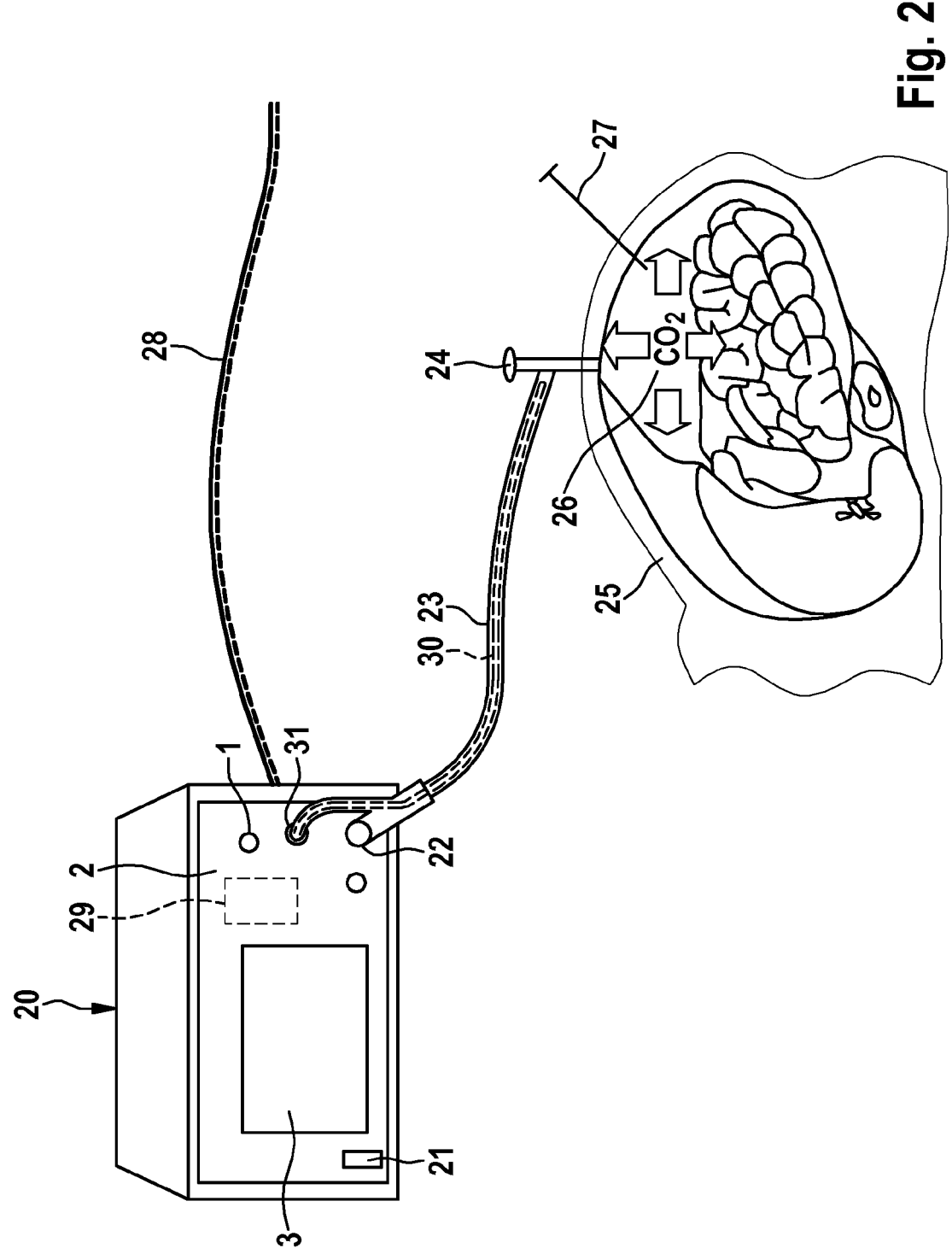
FIG. 2 shows an exemplary embodiment of a medical insufflation device according to the invention, comprising a measuring device in accordance with FIG. 1.

As depicted schematically in FIG. 2, a medical insufflation device in accordance with one exemplary embodiment of the invention comprises a medical insufflation machine 20, the front plate 2 of which has operating and indication elements, for example a display 3 and a power switch 21. Inserted into the front plate 2 of the insufflation machine 20 is a temperature sensing device 1, which is embodied as described above and which, with the end thereof remote from the machine, protrudes over the front plate 2 by approximately 15 mm toward the front. Arranged in the interior of the housing of the insufflation machine 20 are valves and/or pumps, and also a control apparatus 29 in order to supply insufflation gas, $CO_2$ in the depicted example, at a suitable pressure and possibly in an already pre-heated state to a patient. Furthermore, the insufflation device comprises an insufflation tube 23 connected to a connector 22, by means of which insufflation tube the insufflation gas is supplied from the insufflation machine 20 to an insufflation instrument, for example to a Veress needle 24, which pierces the abdominal wall 25 of the patient. The Veress needle 24 is used to introduce $CO_2$ into the abdominal cavity 26 of the patient, as indicated by the blocked arrows, in order to produce a sufficient cavity for performing an endoscopic intervention. FIG. 2 indicates further endoscopic instruments 27 symbolically, which instruments are used in the intervention performed under endoscopic view. A heating apparatus in the form of a heating wire 30 is integrated into the insufflation tube 23, which heating wire can be stretched within the insufflation tube 23 or else extend in the form of a heating coil; as a result of this, the insufflation gas supplied to the patient can be heated. The heating wire 30 is connected to an appropriate electric connector 31 of the insufflation machine 20.

The control apparatus is also embodied to control the further functions of the insufflation machine 20, for example to control or regulate the through-flow and the pressure. The insufflation machine is operated by means of the display 3, which is embodied as a touchscreen. FIG. 2 symbolically indicates a supply tube 28 for supplying the insufflation gas from an external gas supply (not depicted here) to the insufflation machine 20.

The ambient temperature $T_a$ of the insufflation machine 20, which is the temperature of a spatial region in front of the front plate 2 of the machine and which is the same as, or at least representative for, the temperature in a spatial region between the insufflation machine 20 and the patient, is registered with the aid of the temperature sensing device 1 as described above. The insufflation tube 23 extends through this region. Depending on the registered ambient temperature $T_a$, the control apparatus actuates the heating apparatus in such a way that, taking into account the heat transfer, dependent thereon, between the surrounding air and the insufflation gas when it passes through the insufflation tube 23 on its way to the patient, the insufflation gas has a predetermined temperature when entering into the abdominal cavity 26 of the patient, for example approximately the body temperature of the patient. Since the question of whether, and to what extent, the temperature of the insufflation gas changes when passing through the insufflation tube 23 depends on the ambient temperature $T_a$ this allows a very exact temperature control of the gas introduced into the abdominal cavity 26 of the patient.

The invention claimed is:

1. A measuring device for registering an ambient temperature $T_a$ of a medical machine, comprising a measuring housing, which is arranged at an outer wall of the machine, at least one remote temperature sensor arranged at a first distance from the machine and at least one near temperature sensor arranged at a second distance from the machine, wherein the first distance is greater than the second distance, wherein the at least one remote temperature sensor and the at least one near temperature sensor are held within the measuring housing, wherein the at least one remote temperature sensor registers a first temperature $T_1$ and the at least one near temperature sensor registers a second temperature $T_2$, and comprising an evaluation apparatus configured to establish the ambient temperature $T_a$ using a difference between the first temperature $T_1$ registered by the at least one remote temperature sensor and the second temperature $T_2$ registered by the at least one near temperature sensor.

2. The measuring device according to claim 1, characterized in that the measuring housing is embodied in an elongate manner in the form of a temperature sensing device extending beyond the outer wall of the machine.

3. The measuring device of claim 2, wherein the measuring housing includes at least a first and a second region, wherein the first region is outside the machine and the second region is inside the machine.

4. The measuring device of claim 3, wherein the at least one remote temperature sensor is arranged within the first region and the at least one near temperature sensor is arranged within second region.

5. The measuring device according to claim 1, characterized in that the measuring housing is closed-off, at least in an outer region arranged outside of the machine.

6. The measuring device according to claim 5, characterized in that the measuring housing has a cylindrical portion in the outer region, which cylindrical portion has a smaller diameter than a cylindrical portion of an inner region arranged within the machine.

7. The measuring device according to claim 1, characterized in that the at least one remote temperature sensor and/or the at least one near temperature sensor is/are arranged at a distance from the inner side of the measuring housing.

8. The measuring device according to claim 1, characterized in that the evaluation apparatus is at least partly held within the measuring housing.

9. The measuring device according to claim 1, characterized in that the at least one remote temperature sensor and the at least one near temperature sensor are arranged on a common carrier circuit board held within the measuring housing.

10. The measuring device according to claim 1, characterized in that the evaluation apparatus is configured to establish the ambient temperature $T_a$ using a thermal resistance $R_{th1}$ between the surroundings of the machine and the at least one remote temperature sensor and a thermal resistance $R_{th2}$ between the at least one remote temperature sensor and the at least one near temperature sensor.

11. The measuring device according to claim 10, characterized in that the evaluation apparatus is configured to establish the ambient temperature $T_a$ in accordance with $$T_a = T_1 + k(T_1 - T_2)$$

where $$k = R_{th1}/R_{th2}.$$

12. The measuring device according to claim 1, characterized in that the measuring device has at least two remote temperature sensors and/or at least two near temperature sensors, and in that the evaluation apparatus is configured to generate an error signal in the case where a deviation $\Delta T_1$ between the temperatures registered by the at least two remote temperature sensors and/or a deviation $\Delta T_2$ between the temperatures registered by the at least two near temperature sensors is/are greater than a pre-determinable threshold $\Delta T_s$.

13. The measuring device according to claim 1, characterized in that the at least one near temperature sensor and the at least one remote temperature sensor are embodied as semiconductor sensors or in that the at least one near temperature sensor and the at least one remote temperature sensor are embodied as infrared sensors or in that at least one near temperature is embodied as a semiconductor sensor and at least one near temperature sensor is embodied as an infrared sensor and/or at least one remote temperature sensor is embodied as a semiconductor sensor and at least one remote temperature sensor is embodied as an infrared sensor.

14. A device for medical insufflation, comprising a medical insufflation machine, an insufflation tube for supplying an insufflation gas from the insufflation machine to a patient, a heating apparatus for the temperature control of the insufflation gas supplied to the patient and a control apparatus for actuating the heating apparatus, characterized in that the insufflation machine has a measuring device for registering an ambient temperature $T_a$ according to claim 1 and in that the control apparatus is configured to actuate the heating apparatus taking into account the registered ambient temperature $T_a$.

15. The device according to claim 14, characterized in that at least two remote temperature sensors and/or at least two near temperature sensors are present for registering the ambient temperature $T_a$, in that the evaluation apparatus is configured to establish a temperature difference $\Delta T_1$, $\Delta T_2$ between two remote temperature sensors and/or between two near temperature sensors and to generate an error signal in the case where at least one temperature difference $\Delta T_1$, $\Delta T_2$ exceeds a pre-determinable threshold $\Delta T_s$, and in that the control apparatus is configured in such a way that the heating apparatus is switched off as a result of the error signal.

16. A measuring method for registering an ambient temperature $T_a$ of a medical machine, wherein a first temperature $T_1$ is measured using at least one remote temperature sensor arranged at a first distance from the machine, within a measuring housing arranged on an outer wall of the machine, and a second temperature $T_2$ is measured using at least one near temperature sensor arranged at a second distance from the machine, also within the measuring housing, wherein the first distance is greater than the second distance, a temperature difference is established and wherein the ambient temperature $T_a$ is established using the temperature difference.

17. The measuring method according to claim 16, characterized in that the ambient temperature $T_a$ is established in accordance with $$T_a = T_1 + k(T_1 - T_2)$$

where $$k = R_{th1}/R_{th2},$$

where k or $R_{th1}$ and $R_{th2}$ were established in advance.

18. A method for medical insufflation, wherein an insufflation gas is supplied to a patient via an insufflation tube using an insufflation machine, the temperature of which insufflation gas being controlled by a heating apparatus, characterized in that an ambient temperature $T_a$ of the insufflation machine is registered using a measuring method according to claim 16 and the heating apparatus is actuated depending on the registered ambient temperature $T_a$.

19. The measuring method of claim 16, wherein the measuring housing comprises at least a first and a second region, wherein the first region is outside the machine and the second region is inside the machine.

20. The measuring method of claim 19, wherein the at least one remote temperature sensor is arranged within the first region and the at least one near temperature sensor is arranged within the second region.

* * * * *